United States Patent
Nicou et al.

(10) Patent No.: US 11,324,682 B2
(45) Date of Patent: May 10, 2022

(54) COMPOSITION FOR DYEING THE HAIR, COMPRISING AN OXIDATION BASE OF PARA-PHENYLENEDIAMINE TYPE AND A 2-AMINO-5-ETHYLPHENOL COUPLER

(71) Applicant: L'OREAL, Paris (FR)

(72) Inventors: Valérie Nicou, Saint-Ouen (FR); Aziz Fadli, Aulnay-sous-bois (FR); Frédéric Le Grand, Saint-Ouen (FR)

(73) Assignee: L'OREAL, Paris (FR)

( * ) Notice: Subject to any disclaimer, the term of this patent is extended or adjusted under 35 U.S.C. 154(b) by 352 days.

(21) Appl. No.: 16/062,207

(22) PCT Filed: Dec. 20, 2016

(86) PCT No.: PCT/EP2016/082000
§ 371 (c)(1),
(2) Date: Jun. 14, 2018

(87) PCT Pub. No.: WO2017/108840
PCT Pub. Date: Jun. 29, 2017

(65) Prior Publication Data
US 2020/0163851 A1   May 28, 2020

(30) Foreign Application Priority Data

Dec. 21, 2015   (FR) ...................................... 1562910

(51) Int. Cl.
| | | |
|---|---|---|
| *A61K 8/20* | (2006.01) | |
| *A61K 8/22* | (2006.01) | |
| *A61Q 5/10* | (2006.01) | |
| *A61K 8/41* | (2006.01) | |
| *A61K 8/34* | (2006.01) | |

(52) U.S. Cl.
CPC ................ *A61K 8/411* (2013.01); *A61K 8/20* (2013.01); *A61K 8/22* (2013.01); *A61K 8/347* (2013.01); *A61K 8/415* (2013.01); *A61K 8/416* (2013.01); *A61Q 5/10* (2013.01); *A61K 2800/88* (2013.01)

(58) Field of Classification Search
None
See application file for complete search history.

(56) References Cited

U.S. PATENT DOCUMENTS

| | | |
|---|---|---|
| 4,003,699 A | 1/1977 | Rose et al. |
| 4,137,180 A | 1/1979 | Naik et al. |
| RE30,199 E | 1/1980 | Rose et al. |
| 4,840,639 A | 6/1989 | Husemeyer et al. |
| 4,874,554 A | 10/1989 | Lange et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,284,003 B1 | 9/2001 | Rose et al. |
| 6,730,789 B1 | 5/2004 | Birault et al. |
| 9,125,834 B2 | 9/2015 | Couroux et al. |
| 9,220,671 B2 | 12/2015 | Ascione et al. |
| 9,370,477 B2 | 6/2016 | Allard et al. |
| 2005/0011016 A1 | 1/2005 | Pasquier et al. |
| 2005/0166335 A1 | 8/2005 | Vidal et al. |
| 2007/0067926 A1 | 3/2007 | Schmitt et al. |
| 2007/0136959 A1 | 6/2007 | Fadli |
| 2007/0143935 A1 | 6/2007 | Fadli et al. |
| 2009/0282622 A1 | 11/2009 | Dahlgren et al. |
| 2012/0180230 A1 | 7/2012 | Schmenger et al. |
| 2012/0210519 A1 | 8/2012 | Lim et al. |
| 2013/0312203 A1 | 11/2013 | Allard et al. |
| 2015/0139925 A1 | 5/2015 | Kamikawa et al. |
| 2015/0283053 A1 | 10/2015 | Odman Schmid et al. |

FOREIGN PATENT DOCUMENTS

| | | | |
|---|---|---|---|
| CA | 2615230 A1 | 4/2008 | |
| CN | 101312707 A | 11/2008 | |
| DE | 2359399 A1 | 6/1975 | |
| DE | 3843892 A1 | 6/1990 | |
| DE | 4133957 A1 | 4/1993 | |
| DE | 19543988 A1 | 5/1997 | |
| DE | 202005014897 U1 | 11/2005 | |
| EP | 0007537 A1 | 2/1980 | |
| EP | 0770375 A1 | 5/1997 | |
| EP | 1550656 A1 | 7/2005 | |
| EP | 1792606 A1 | 6/2007 | |
| EP | 1792903 A1 | 6/2007 | |
| FR | 2733749 A1 | 11/1996 | |

(Continued)

OTHER PUBLICATIONS

Final Office Action for co-pending U.S. Appl. No. 16/062,282, dated Oct. 22, 2019.
Non-Final Office Action for copending U.S. Appl. No. 16/062,282, dated Feb. 28, 2020.
Final Office Action for copending U.S. Appl. No. 16/062,282, dated Jul. 30, 2020.

(Continued)

*Primary Examiner* — Alton N Pryor
(74) *Attorney, Agent, or Firm* — The Marbury Law Group, PLLC

(57) ABSTRACT

The present invention relates to a composition for dyeing keratin fibres, comprising: (a) at least one 2-amino-5-ethylphenol coupler, or an addition salt or solvate thereof, and (b) at least one oxidation base 3-(2,5-diaminophenyl)-1-propanol and/or the addition salts thereof or solvates thereof. The invention also relates to a process for dyeing keratin fibres using this composition. Finally, the invention relates to the use of such a composition for dyeing keratin fibres, and in particular the hair.

14 Claims, No Drawings

(56) References Cited

FOREIGN PATENT DOCUMENTS

| | | |
|---|---|---|
| FR | 2750048 A1 | 12/1997 |
| FR | 2801308 A1 | 5/2001 |
| FR | 2886136 A1 | 12/2006 |
| FR | 2893027 A1 | 5/2007 |
| FR | 2988594 A1 | 10/2013 |
| GB | 1026978 A | 4/1966 |
| GB | 1153196 A | 5/1969 |
| JP | 02-019576 A | 1/1990 |
| JP | 05-163124 A | 6/1993 |
| JP | 2015-512367 A | 4/2015 |
| WO | 8000214 A1 | 2/1980 |
| WO | 94/08969 A1 | 4/1994 |
| WO | 94/08970 A1 | 4/1994 |
| WO | 96/15765 A1 | 5/1996 |
| WO | 01/35917 A1 | 5/2001 |
| WO | 2004/041225 A1 | 5/2004 |
| WO | 2007/034410 A1 | 3/2007 |
| WO | 2010/133640 A2 | 11/2010 |
| WO | 2012/080289 A2 | 6/2012 |
| WO | 2013/152956 A1 | 10/2013 |
| WO | 2017/108841 A1 | 6/2017 |
| WO | 2017/108847 A1 | 6/2017 |

OTHER PUBLICATIONS

Non-Final Office Action for copending U.S. Appl. No. 16/063,719, dated Sep. 18, 2020.
Translation of Chinese Office Action for counterpart Application No. 201680074384.9, dated Jul. 24, 2020.
International Search Report for counterpart Application No. PCT/EP2016/082001, dated Mar. 28, 2017.
International Search Report for counterpart Application No. PCT/EP2016/082011, dated May 15, 2017.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Translated Chinese Office Action for counterpart Application No. 201680074386.8, dated Jun. 28, 2020.
Translated Chinese Office Action for counterpart Application No. 201680074381.5, dated Aug. 10, 2020.
Non-Final Office Action for co-pending U.S. Appl. No. 16/062,282, dated Jun. 12, 2019.
Translation of Japanese Office Action for counterpart Application No. 2019-145549, dated Oct. 19, 2020.
Notice of Reasons for Refusal for counterpart JP Application No. 2018-532092, dated May 7, 2019 with Translation.
Notice of Reasons for Refusal for counterpart JP Application No. 2018-532093, dated Jul. 1, 2019 with Translation.
Notice of Reasons for Refusal for counterpart JP Application No. 2018-532094, dated May 7, 2019 with Translation.
International Search Report for Application No. PCT/EP2016/08200, dated Mar. 28, 2017.
Final Office Action for copending U.S. Appl. No. 16/062,282, dated Nov. 5, 2021.
Non-Final Office Action for copending U.S. Appl. No. 16/062,282, dated May 28, 2021.

COMPOSITION FOR DYEING THE HAIR, COMPRISING AN OXIDATION BASE OF PARA-PHENYLENEDIAMINE TYPE AND A 2-AMINO-5-ETHYLPHENOL COUPLER

CROSS REFERENCE TO RELATED APPLICATIONS

This is a national stage application of PCT/EP2016/082000, filed internationally on Dec. 20, 2016, which claims priority to French Application No. 1562910, filed on Dec. 21, 2015, both of which are incorporated by reference herein in their entireties.

The present invention relates to a composition for dyeing keratin fibres, comprising a particular para-phenylenediamine oxidation base and a 2-amino-5-ethylphenol coupler.

The invention also relates to a process for dyeing keratin fibres using this composition.

Finally, the invention relates to the use of such a composition for dyeing keratin fibres, and in particular the hair.

Many people have sought for a long time to modify the colour of their hair and in particular to mask their grey hair.

It is known practice to dye keratin fibres, in particular human keratin fibres such as the hair, to obtain "permanent" colourings with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds which, when combined with oxidizing products, may give rise to coloured compounds via a process of oxidative condensation.

It is also possible to vary the shades obtained with these oxidation bases by combining them with couplers or colour modifiers. The variety of molecules used as oxidation bases and couplers allows a wide range of colours to be obtained.

However, the use of these dye compositions may have a certain number of drawbacks.

Specifically, after application to keratin fibres, the dyeing power obtained may not be entirely satisfactory, or may even be weak, and lead to a restricted range of colours.

The colourings may also not be sufficiently persistent with respect to external agents such as light, shampoo or perspiration, and may also be too selective, i.e. the difference in colouring is too great along the same keratin fibre that is differently sensitized between its end and its root.

Oxidation bases of the para-phenylenediamine type are commonly used in the field of hair dyeing.

It is known practice, for example, to use 3-(2,5-diaminophenyl)-1-propanol (or 2-γ-hydroxypropyl-para-phenylenediamine) in oxidation dyeing, in particular in document WO 80/00214.

By way of example, the 2-amino-5-ethylphenol coupler is known from document DE202005014897. In said document, it is combined with another m-aminophenol coupler and oxidation bases for dyeing their hair in a varied manner. According to said document, it is possible, with such a combination, to obtain uniform colourations from the root to the end of the hair.

There is a real need to provide a composition for dyeing keratin fibres, in particular human keratin fibres such as the hair, which does not have the drawbacks mentioned above, i.e. which is capable of leading to a colouration which exhibits strong colouration with improved fastness and also good coverage of grey hair.

These aims and others are achieved by the present invention, one subject of which is thus a composition for dyeing keratin fibres, comprising:
(a) at least one 2-amino-5-ethylphenol coupler, or an addition salt or solvate thereof, and
(b) at least one oxidation base 3-(2,5-diaminophenyl)-1-propanol and/or the addition salts thereof or solvates thereof.

Another subject of the present invention is a process for dyeing keratin fibres in which the composition according to the invention is applied to said fibres.

The invention also relates to the use of said composition for dyeing keratin fibres, and in particular the hair.

This composition gives particularly good coverage of depigmented keratin fibres such as grey hair.

The composition according to the invention makes it possible to produce particularly intense and sparingly selective colourations, i.e. colourations that are uniform along the length of the fibre.

Moreover, the colourings obtained by means of the composition according to the invention withstand the various attacking factors to which the hair may be subjected, such as light, bad weather, washing and perspiration.

Other subjects, characteristics, aspects and advantages of the invention will emerge even more clearly on reading the description and the examples that follow.

In that which follows and unless otherwise indicated, the limits of a range of values are included within this range, in particular in the expressions "of between" and "ranging from . . . to . . . ".

In the context of the present invention, the expression "at least one" is equivalent to the expression "one or more".

The present invention also covers the mesomeric forms and the stereoisomers of the various oxidation dyes of use for the invention.

In the context of the invention, and unless indicated otherwise, the term "alkyl" used for the alkyl radicals and also for the groups comprising an alkyl part means a linear or branched carbon-based chain comprising from 1 to 4 carbon atoms, which is unsubstituted or substituted with one or more heterocycles, or with one or more phenyl groups or with one or more groups chosen from halogen atoms such as chlorine, bromine, iodine and fluorine; hydroxyl, alkoxy, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri($C_1$-$C_4$)alkylammonium radicals, or alternatively with a di($C_1$-$C_4$)alkylamino radical in which the two alkyl groups may form, together with the nitrogen atom of said di($C_1$-$C_4$)alkylamino group to which they are attached, a ring that may be interrupted with one or more nitrogen, oxygen or sulfur atoms.

Similarly, according to the invention, the term "alkoxy" used for the alkoxy radicals and also for the groups comprising an alkoxy part means a linear or branched O-carbon-based chain comprising from 1 to 4 carbon atoms, which is unsubstituted or substituted with one or more groups chosen from heterocycles; halogen atoms such as chlorine, bromine, iodine and fluorine; hydroxyl, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri ($C_1$-$C_4$)alkylammonium radicals, or alternatively with a di($C_1$-$C_4$)alkylamino radical in which the two alkyl groups may form, together with the nitrogen atom of said di($C_1$-$C_4$)alkylamino group to which they are attached, a ring that may be interrupted with one or more nitrogen, oxygen or sulfur atoms.

According to the invention, the term "heterocycle" is intended to mean an aromatic or non-aromatic 5-, 6-, 7- or 8-membered ring containing from 1 to 3 heteroatoms chosen from nitrogen, sulfur and oxygen atoms. These heterocycles may be fused to other heterocycles or to a phenyl group. They may be substituted with a halogen atom; a ($C_1$-$C_4$) alkyl radical; a ($C_1$-$C_4$)alkoxy radical; a hydroxyl radical; an amino radical; a ($C_1$-$C_4$)alkylamino radical; a di($C_1$-$C_4$) alkylamino radical in which the two alkyl groups may form, together with the nitrogen atom to which they are attached, a ring that may be interrupted with one or more nitrogen, oxygen or sulfur atoms. These heterocycles may also be quaternized with a ($C_1$-$C_4$)alkyl radical.

(a) The 2-amino-5-ethylphenol Coupler

The composition according to the invention comprises one or more 2-amino-5-ethylphenol couplers, in free form, or addition salts thereof or solvates thereof.

The addition salts are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates more particularly represent the hydrates of the 2-amino-5-ethylphenol coupler and/or the combination of the 2-amino-5-ethylphenol coupler with a linear or branched $C_1$ to $C_4$ alcohol such as methanol, ethanol, isopropanol or n-propanol. Preferably, the solvates are hydrates.

The total amount of the 2-amino-5-ethylphenol coupler or an addition salt or solvate thereof, present in the composition according to the invention, can range from 0.0001% to 20% by weight, preferably from 0.005% to 10% by weight, and more preferentially from 0.01% to 6% by weight, relative to the total weight of the composition.

Oxidation Bases

The composition according to the invention comprises one or more 3-(2,5-diaminophenyl)-1-propanol bases in free form, or the addition salts thereof or solvates thereof such as hydrates.

The addition salts are in particular chosen from addition salts with an acid, such as hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, ammonia, amines or alkanolamines.

Moreover, the solvates more particularly represent the hydrates of 3-(2,5-diaminophenyl)-1-propanol or the combination of 3-(2,5-diaminophenyl)-1-propanol with a linear or branched $C_1$ to $C_4$ alcohol such as methanol, ethanol, isopropanol or n-propanol. Preferably, the solvates are hydrates.

The total amount of 3-(2,5-diaminophenyl)-1-propanol or the addition salts or solvates thereof, present in the composition according to the invention, can range from 0.0001% to 20% by weight, preferably from 0.005% to 10% by weight, and more preferentially from 0.01% to 6% by weight, relative to the total weight of the composition.

Additional Couplers and Bases

The composition of the invention may contain other additional couplers and oxidation bases. Among these couplers other than the 2-amino-5-ethylphenol of use for the invention, mention may in particular be made of meta-phenylenediamines, meta-aminophenols other than 2-amino-5-ethylphenol, meta-diphenols, naphthalene couplers, heterocyclic couplers, the addition salts thereof, solvates thereof and mixtures thereof.

Among the couplers that can be used in the composition according to the invention, mention may particularly be made of 6-hydroxybenzomorpholine, 1,3-dihydroxybenzene, 2-methyl-1,3-dihydroxybenzene, 1-hydroxy-3-aminobenzene, 2-methyl-5-hydroxyethylaminophenol, 2,4-diaminophenoxyethanol, 4-amino-2-hydroxytoluene, 2,4-dichloro-3-aminophenol, 5-amino-4-chloro-o-cresol, 5-amino-6-chloro-o-cresol, 4-chloro-1,3-dihydroxybenzene, 1β-hydroxyethyloxy-2,4-diaminobenzene, 2-amino-4-(β-hydroxyethylamino)-1-methoxybenzene, 1,3-bis(2,4-diaminophenoxy) propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy N-methylindole, 2-amino-3-hydroxypyridine, 3,5-diamino-2,6-dimethoxypyridine, 2,6-dihydroxy-3-4-dimethylpyridine, 3-amino-2-methylamino-6-methoxypyridine, 6-hydroxybenzomorpholine, 1-N-(β-hydroxyethyl) amino-3,4-methylenedioxybenzene, 2,6-bis(I3-hydroxyethylamino)toluene, 3-methyl-1-phenyl 5-pyrazolone, the addition salts thereof with an acid and the solvates thereof.

Preferably, the additional coupler(s) present in the composition according to the invention are chosen from 6-hydroxybenzomorpholine, 2,4-diaminophenoxyethanol, 1,3-dihydroxybenzene, 1-hydroxy-3-aminobenzene, 2-methyl-5-hydroxyethylaminophenol, 2-methyl-1,3-dihydroxybenzene, 2-amino-3-hydroxypyridine, the addition salts thereof, solvates thereof and mixtures thereof.

The total amount of the coupler(s) present in the composition according to the invention can range from 0.0001% to 20% by weight, preferably from 0.005% to 10% by weight and more preferentially from 0.01% to 6% by weight relative to the total weight of the composition.

Among the additional oxidation bases, mention may be made of para-phenylenediamines other than the 3-(2,5-diaminophenyl)-1-propanol, bis(phenyl)alkylenediamines, para-aminophenols, bis-para-aminophenols, ortho-aminophenols and heterocyclic bases, and the addition salts thereof and solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis)β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-paraphenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid and solvates thereof.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof with an acid and solvates thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid and solvates thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid and solvates thereof.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the 3-aminopyrazolo[1,5-a]pyridine bases, it will in particular be preferred to use 2[(3-aminopyrazolo[1,5-a]pyridin-2-yl)oxy]ethanol, and/or 4-(3-aminopyrazolo[1,5-a]pyridin-2-yl)-1,1-dimethylpiperazin-1-ium chloride and/or the corresponding addition salts or solvates thereof.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-(β-methoxyethyl)pyrazole.

Among the pyrazole derivatives, a 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Among the heterocyclic bases, use will preferably be made of 4,5-diamino-1-(β-hydroxyethyl)pyrazole and/or 2,3-diamino-6,7-dihydro-1H,5H-pyrazolo[1,2-a]pyrazol-1-one and/or 2[(3-aminopyrazolo[1,5-a]pyridin-2-yl)oxy]ethanol and/or 4-(3-aminopyrazolo[1,5-a]pyridin-2-yl)-1,1-dimethylpiperazin-1-ium chloride and/or the corresponding salts or solvates thereof.

The total amount of oxidation base(s) present in the composition according to the invention can range from 0.0001% to 20% by weight, preferably from 0.005% to 10% by weight and more preferentially from 0.01% to 6% by weight relative to the total weight of the composition.

Surfactants

The composition according to the invention may optionally also comprise one or more surfactants.

The surfactant(s) that may be used in the composition according to the invention may be chosen from non-ionic, cationic, anionic and amphoteric or zwitterionic surfactants.

The composition according to the invention may comprise one or more non-ionic surfactants.

The non-ionic surfactants that may be used are described, for example, in the *Handbook of Surfactants* by M. R. Porter, published by Blackie & Son (Glasgow and London), 1991, pp. 116-178.

Examples of non-ionic surfactants that may be mentioned include the following non-ionic surfactants:
oxyalkylenated (C8-C24)alkylphenols;
saturated or unsaturated, linear or branched, oxyalkylenated or glycerolated $C_8$-$C_{40}$ alcohols, comprising one or two fatty chains;
saturated or unsaturated, linear or branched, oxyalkylenated $C_8$ to $C_{30}$ fatty acid amides;
esters of saturated or unsaturated, linear or branched, $C_8$ to $C_{30}$ acids and of polyethylene glycols;
preferably oxyethylenated esters of saturated or unsaturated, linear or branched, $C_8$ to $C_{30}$ acids and of sorbitol;
esters of fatty acids and of sucrose;
($C_8$-$C_{30}$)alkyl(poly)glucosides and ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;
saturated or unsaturated oxyethylenated vegetable oils;
condensates of ethylene oxide and/or of propylene oxide;
N-($C_8$-$C_{30}$)alkylglucamine and N-($C_8$-$C_{30}$)acylmethylglucamine derivatives;
aldobionamides;
amine oxides;
oxyethylenated and/or oxypropylenated silicones;
and mixtures thereof.

The oxyalkylene units are more particularly oxyethylene or oxypropylene units, or their combination, preferably oxyethylene units.

The number of moles of ethylene oxide and/or propylene oxide preferably ranges from 1 to 250, more particularly from 2 to 100 and better still from 2 to 50; the number of moles of glycerol ranges in particular from 1 to 50 and better still from 1 to 10.

Advantageously, the non-ionic surfactants according to the invention do not comprise any oxypropylene units.

By way of example of glycerolated non-ionic surfactants, use may preferably be made of monoglycerolated or polyglycerolated $C_8$ to $O_{40}$ alcohols comprising from 1 to 50 mol of glycerol, preferably from 1 to 10 mol of glycerol.

As examples of compounds of this type, mention may be made of lauryl alcohol containing 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol containing 2 mol of glycerol, cetearyl alcohol containing 6 mol of glycerol, oleyl/cetyl alcohol containing 6 mol of glycerol, and octadecanol containing 6 mol of glycerol.

Among the glycerolated alcohols, it is more particularly preferred to use a C8/C10 alcohol containing 1 mol of glycerol, a C10/C12 alcohol containing 1 mol of glycerol and a C12 alcohol containing 1.5 mol of glycerol.

The non-ionic surfactant(s) that may be used in the composition according to the invention are preferentially chosen from:
oxyethylenated $C_8$ to $O_{40}$ alcohols comprising from 1 to 100 mol of ethylene oxide, preferably from 2 to 50 and more particularly from 2 to 40 mol of ethylene oxide and comprising one or two fatty chains;
saturated or unsaturated oxyethylenated plant oils comprising from 1 to 100 and preferably from 2 to 50 mol of ethylene oxide;
($C_8$-$C_{30}$)alkyl(poly)glucosides, which are optionally oxyalkylenated (0 to 10 OE) and comprising 1 to 15 glucose units;
monoglycerolated or polyglycerolated $C_8$ to $C_{40}$ alcohols, comprising from 1 to 50 mol of glycerol and preferably from 1 to 10 mol of glycerol;
saturated or unsaturated, linear or branched, oxyalkylenated $C_8$ to $C_{30}$ fatty acid amides;
esters of saturated or unsaturated, linear or branched, $C_8$ to $C_{30}$ acids and of polyethylene glycols;
and mixtures thereof.

The composition according to the invention may comprise one or more cationic surfactants.

The term "cationic surfactant" is intended to mean a surfactant that is positively charged when it is contained in the composition according to the invention. This surfactant may bear one or more positive permanent charges or may contain one or more cationizable functions in the composition according to the invention.

The cationic surfactant(s) are preferably chosen from primary, secondary or tertiary fatty amines, which are optionally polyoxyalkylenated, or salts thereof, and quaternary ammonium salts, and mixtures thereof.

The fatty amines generally comprise at least one $C_8$ to $C_{30}$ hydrocarbon-based chain.

Mention may be made, as quaternary ammonium salts, for example, of:
quaternary ammonium salts such as tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is preferable in particular to use the chloride salts of these compounds.

quaternary ammonium salts of imidazoline, for example sold under the name Rewoquat® W 75 by the company Rewo;

di- or triquaternary ammonium salts, for example, Finquat CT-P available from the company Finetex (Quaternium 89), and Finquat CT, available from the company Finetex (Quaternium 75);

quaternary ammonium salts containing at least one ester function, such as the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

Such compounds are sold, for example, under the names Dehyquart® by the company Henkel, Stepanquat® by the company Stepan, Noxamium® by the company CECA or Rewoquat® WE 18 by the company Rewo-Witco.

Use may also be made of the ammonium salts containing at least one ester function that are described in patents U.S. Pat. Nos. 4,874,554 and 4,137,180.

Use may be made of behenoylhydroxypropyltrimethylammonium chloride sold by KAO under the name Quatarmin BTC 131.

Preferably, the ammonium salts comprising at least one ester function comprise two ester functions.

Among the quaternary ammonium salts containing at least one ester function, which may be used, it is preferred to use dipalmitoylethylhydroxyethylmethylammonium salts.

The composition according to the invention may comprise one or more anionic surfactants.

The term "anionic surfactant" is intended to mean a surfactant comprising, as ionic or ionizable groups, only anionic groups. These anionic groups are preferably chosen from the groups —COOH, —COO⁻, —SO$_3$H, —SO$_3^-$, —OSO$_3$H, —OSO$_3^-$, —PO$_2$H$_2$, —PO$_2$H⁻, —PO$_{22}^-$, —P(OH)$_2$, =P(O)OH, —P(OH)O⁻, =P(O)O⁻, =POH, =PO⁻, the anionic parts comprising a cationic counterion such as those of an alkali metal, an alkaline-earth metal or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglucoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 40 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglucosidepolycarboxylic acids may be chosen from $C_6$-$C_{24}$ alkyl polyglucoside-citrates, $C_6$-$C_{24}$ alkyl polyglucoside-tartrates and $C_6$-$C_{24}$ alkyl polyglucoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may in particular be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Use is preferably made of alkali metal or alkaline-earth metal salts and in particular of sodium or magnesium salts.

Among the anionic surfactants mentioned, ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds, are preferably used.

In particular, ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds, are preferably used. Even better still, it is preferred to use sodium lauryl ether sulfate containing 2.2 mol of ethylene oxide.

The composition according to the invention may comprise one or more amphoteric or zwitterionic surfactants.

In particular, the amphoteric or zwitterionic surfactant(s), which are preferably non-silicone, which may be used in the composition according to the present invention may in particular be derivatives of optionally quaternized aliphatic secondary or tertiary amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

Mention may in particular be made of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized, secondary or tertiary aliphatic amine derivatives that can be used, mention may be made of the compounds classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Mention may be made of the compound classified in the CTFA dictionary under the name sodium diethylaminopropyl cocoaspartamide and sold by the company Chimex under the name Chimexane HB.

These compounds may be used alone or as mixtures.

Among the amphoteric or zwitterionic surfactants mentioned above, use is preferably made of ($C_8$-$C_{20}$)alkylbetaines such as cocoylbetaine, $(C_8-C_{20})$alkylamido$(C_3-C_8)$ alkylbetaines such as cocamidopropylbetaine, and mixtures thereof, and the compounds of formula (VIII) such as the sodium salt of diethylaminopropyl laurylaminosuccinamate (INCI name: sodium diethylaminopropyl cocoaspartamide).

Preferably, the composition according to the invention comprises one or more surfactants. More preferentially, the composition according to the invention comprises one or more surfactants chosen from non-ionic, anionic or amphoteric surfactants.

Particularly preferably, the composition according to the invention comprises one or more non-ionic surfactants.

The total amount of surfactant(s), present in the composition according to the invention, can range from 0.1% to 25% by weight, and preferably from 0.5% to 20% by weight, relative to the total weight of the composition.

Alkaline Agents

The composition according to the invention may optionally also comprise one or more alkaline agents.

Preferably, the dye composition comprises one or more organic or mineral alkaline agents.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the highest basicity function. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (IX) below:

in which formula (IX) W is a divalent $C_1$ to $C_6$ alkylene radical optionally substituted with one or more hydroxyl groups or a $C_1$ to $C_6$ alkyl radical and/or optionally interrupted with one or more heteroatoms, such as O, or $NR_u$, and $R_x$, $R_y$, $R_z$, $R_t$ and $R_u$, which are identical or different, represent a hydrogen atom or a $C_1$ to $C_6$ alkyl, $C_1$ to $C_6$ hydroxyalkyl or $C_1$ to $C_6$ aminoalkyl radical.

Examples of amines of formula (IX) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are, for example, histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made in particular of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino (imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition according to the invention are chosen from aqueous ammonia, alkanolamines and amino acids in neutral or ionic form, in particular basic amino acids.

More preferentially, the alkaline agent(s) present in the composition according to the invention are chosen from aqueous ammonia, alkanolamines, and mixtures thereof. According to one particular embodiment, the alkaline agent is an organic agent, preferably an alkanolamine. When the alkaline agent is an alkanolamine, it is chosen from monoethanolamine.

The total amount of alkaline agent(s) present in the composition according to the invention may range from 0.01% to 30% by weight, and preferably from 0.1% to 20% by weight relative to the total weight of the ready-to-use composition.

The composition according to the invention may optionally also comprise one or more organic solvents.

By way of organic solvent, mention may for example be made of linear or branched $C_2$ to $C_4$ alkanols, such as ethanol and isopropanol; glycerol; polyols and polyol ethers such as 2-butoxyethanol, propylene glycol, hexylene glycol, dipropylene glycol, propylene glycol monomethyl ether, and diethylene glycol monoethyl ether and monomethyl ether, and also aromatic alcohols or ethers, such as benzyl alcohol or phenoxyethanol, and mixtures thereof.

The organic solvent(s) may be present in an amount ranging from 0.01% to 30% by weight, preferably ranging from 2% to 25% by weight, relative to the total weight of the composition.

The composition according to the invention may also optionally comprise one or more additives, different from the compounds of the invention and among which mention may be made of cationic, anionic, non-ionic or amphoteric polymers or mixtures thereof, antidandruff agents, antiseborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, in particular polymeric thickeners, opacifiers or nacreous agents, antioxidants, hydroxy acids, fragrances, preservatives, pigments and ceramides.

Needless to say, those skilled in the art will take care to select this or these optional additional compound(s) such that the advantageous properties intrinsically associated with the composition according to the invention are not, or are not substantially, adversely affected by the envisaged addition(s).

The above adjuvants may generally be present in an amount comprised, for each of them, of between 0 and 20% by weight relative to the total weight of the ready-to-use composition.

Chemical Oxidizing Agent

According to one particular embodiment of the invention, the composition according to the invention comprises at least one chemical oxidizing agent.

The expression "chemical oxidizing agent" is intended to mean an oxidizing agent other than atmospheric oxygen.

In particular, the chemical oxidizing agent(s) are chosen, for example, from hydrogen peroxide, urea peroxide, alkali metal bromates, peroxygenated salts, such as for example persulfates or perborates, peracids and precursors thereof and alkali metal or alkaline-earth metal percarbonates. Advantageously, the oxidizing agent is hydrogen peroxide.

The chemical oxidizing agent(s) may be present in a content ranging from 0.5% to 20%, better still from 1% to 15% by weight relative to the total weight of the dye composition.

When the composition of the invention contains at least one alkaline agent and at least one oxidizing agent, the composition is then ready to use. It can be applied to the hair so as to allow the keratin fibres to be dyed.

Fatty Substances

According to one particular embodiment, the composition according to the invention comprises one or more fatty substances different from salified fatty acids.

The term "fatty substance" is intended to mean an organic compound that is insoluble in water at ambient temperature (25° C.) and at atmospheric pressure ($1.013 \times 10^5$ Pa) (solubility of less than 5% by weight, and preferably less than 1% by weight, even more preferably less than 0.1% by weight). They bear in their structure at least one hydrocarbon-based chain comprising at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The term "oil" is intended to mean a "fatty substance" that is liquid at ambient temperature (25° C.) and at atmospheric pressure ($1.013 \times 10^5$ Pa).

The term "non-silicone fatty substance" is intended to mean a fatty substance not containing any Si—O bonds and the term "silicone fatty substance" is intended to mean a fatty substance containing at least one Si—O bond.

The fatty substances used in the composition according to the invention are different from salified fatty acids, i.e. they can be present in the composition in the form of free fatty acids.

In other words, the fatty substances of the invention do not contain any salified carboxylic acid groups (—C(O)O—). Particularly, the fatty substances of the invention are neither polyoxyalkylenated nor polyglycerolated.

Preferably, the fatty substances are different from salified fatty acids.

Preferably, the composition according to the invention comprises one or more fatty substances that are liquid at ambient temperature and atmospheric pressure ($1.013 \times 10^5$ Pa), different from salified fatty acids.

More particularly, the liquid fatty substances according to the invention are chosen from $C_6$-$C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid fatty acid and/or fatty alcohol esters other than triglycerides, and silicone oils, and mixtures thereof.

It is recalled that the fatty alcohols and esters more particularly contain at least one saturated or unsaturated, linear or branched hydrocarbon-based group, comprising 6 to 30 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, they are linear, branched or optionally cyclic, and are preferably alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil, and mixtures thereof.

The liquid fatty alcohols that are suitable for use in the invention are more particularly chosen from linear or branched, saturated or unsaturated, preferably unsaturated or branched, alcohols comprising from 6 to 30 carbon atoms and preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols other than the triglycerides mentioned above, mention may be made in particular of esters of saturated or unsaturated, linear $C_1$ to $C_{26}$ or branched $C_3$ to $C_{26}$ aliphatic monoacids or polyacids and of saturated or unsaturated, linear $C_1$ to $C_{26}$ or branched $C_3$ to $C_{26}$ aliphatic monoalcohols or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononate; octyldodecyl erucate; oleyl erucate; ethyl palmitate, isopropyl palmitate, 2-ethylhexyl palmitate, 2-octyldecyl palmitate, alkyl myristates such as isopropyl 2-octyldodecyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of $C_4$ to $C_{22}$ dicarboxylic or tricarboxylic acids and of $C_1$ to $C_{22}$ alcohols and esters of mono-, di- or tricarboxylic acids and of $C_2$ to $C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$ to $C_{30}$ and preferably $C_{12}$ to $C_{22}$ fatty acids. It is recalled that the term "sugar" is intended to mean oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof such as, in particular, the mixed esters oleo-palmitate, oleo-stearate and palmito-stearate.

More particularly, use is made of monoesters and diesters and in particular sucrose, glucose or methylglucose mono- or dioleates, stearates, behenates, oleopalmitates, linoleates, linolenates and oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the composition according to the present invention may be volatile or non-volatile, cyclic, linear or branched silicones, which are unmodified or modified with organic groups, and preferably have a viscosity from $5 \times 10^{-6}$ to 2.5 m$^2$/s at 25° C., and preferably $1 \times 10^{-5}$ to 1 m$^2$/s.

Preferably, the silicone oils are chosen from polydialkylsiloxanes, in particular polydimethylsiloxanes (PDMS), and liquid polyorganosiloxanes comprising at least one aryl group.

These silicone oils can also be organomodified. The organomodified silicone oils that may be used in accordance with the invention are preferably liquid silicones as defined above and comprising in their structure one or more organofunctional groups attached via a hydrocarbon-based group, chosen, for example, from amine groups and alkoxy groups.

Organopolysiloxanes are defined in greater detail in Walter Noll's *Chemistry and Technology of Silicones* (1968), Academic Press. They may be volatile or non-volatile.

When they are volatile, the silicone oils are more particularly chosen from those with a boiling point of between 60° C. and 260° C., and even more particularly from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile polydialkylsiloxanes are preferably used.

These silicone oils are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 mm$^2$/s;
- the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

The organomodified silicones that may be used in accordance with the invention are silicones as defined above and comprising in their structure one or more organofunctional groups attached via a hydrocarbon-based group.

As regards the liquid polyorganosiloxanes comprising at least one aryl group, they may in particular be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:
- the Silbione® oils of the 70 641 series from Rhodia;
- oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may be made of polyorganosiloxanes comprising:
- substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$ to $C_4$ aminoalkyl groups;
- alkoxy groups,
- hydroxyl groups.

The liquid fatty substance(s) is (are) preferentially chosen from liquid hydrocarbons containing more than 16 carbon atoms, vegetable oils, liquid fatty alcohols and liquid fatty esters, silicone oils and mixtures thereof.

Preferentially, the liquid fatty substance(s) is (are) chosen from liquid hydrocarbons comprising more than 16 carbon atoms, in particular liquid petroleum jelly.

In this particular embodiment, preferably, the total amount of fatty substance(s) present in the composition according to the invention is greater than or equal to 20% by weight, more preferentially greater than or equal to 30% by weight, and better still greater than or equal to 35% by weight, relative to the total weight of the composition.

More preferentially, in this particular embodiment, the total amount of fatty substance(s) present in the composition according to the invention ranges from 30% to 80%, and preferably from 30% to 70% by weight relative to the total weight of the composition.

Even more preferentially, in this particular embodiment, the total amount of liquid fatty substance(s) present in the composition according to the invention is greater than or equal to 20% by weight, more preferentially greater than or equal to 30% by weight, and better still greater than or equal to 35% by weight, relative to the total weight of the composition.

Even better still, in this particular embodiment, the total amount of liquid fatty substance(s) present in the composition according to the invention ranges from 30% to 80%, and preferably from 30% to 70% by weight relative to the total weight of the composition.

When the composition of the invention contains the alkaline agent and the oxidizing agent, it preferably contains at least 20% of fatty substances, preferably liquid fatty substances, preferably at least 30% by weight relative to the total weight of the composition. Preferably, this ready-to-use composition contains between 30% and 55% of fatty substances, preferably liquid fatty substances, preferably between 35% and 50%.

Process of the Invention

Another subject of the invention is a process for dyeing human keratin fibres, in particular the hair, comprising the application to the keratin fibres of the composition according to the invention.

According to one preferred embodiment, the composition contains at least one alkaline agent and at least one oxidizing agent. The composition is then applied to the keratin fibres and left on for approximately 3 to 50 minutes, preferably approximately 5 to 40 minutes, then there follows a step of rinsing, washing with a shampoo, again rinsing and, finally, drying.

If the composition of the invention is not mixed before application with the alkaline agent and the oxidizing agent, the various compositions can be applied sequentially, in any order, with or without intermediate rinsing.

According to another embodiment, the composition according to the invention results from the mixing of at least two compositions:
- a dye composition comprising at least one oxidation base of formula (I), (II) or (III) described above, at least one 2-amino-5-ethylphenol coupler and at least one alkaline agent, and an oxidising composition comprising one or more chemical oxidizing agents.

Multi-Compartment Device

Another subject of the invention is a multi-compartment device, preferably comprising at least two compartments, for dyeing keratin fibres, at least one first compartment containing the dye composition (A) according to the invention and at least one second compartment containing the oxidizing composition (B) as described above.

Finally, the present invention relates to the use of a composition as described above, for dyeing keratin fibres, and in particular the hair.

According to the present application, the term "keratin fibres" denotes human keratin fibres and in particular the hair.

The examples that follow serve to illustrate the invention without, however, being limiting in nature.

EXAMPLES

Example 1

In the examples that follow, all the amounts are given as percentages by weight relative to the total weight of the composition. Unless otherwise indicated, the amounts are indicated in g % of Active Material.

| Dye composition | formula 1 | formula 2 |
|---|---|---|
| SODIUM METABISULFITE | 0.45 | 0.45 |
| ETHANOLAMINE | 4.38 | 4.38 |
| EDTA | 0.2 | 0.2 |
| HYDROXYBENZOMORPHOLINE | 0.006 | — |
| 2-METHYLRESORCINOL | — | 0.18 |
| 6-HYDROXYINDOLE | — | 0.034 |
| 2-AMINO-3-HYDROXYPYRIDINE | — | 0.014 |
| RESORCINOL | 0.2 | 0.5 |
| m-AMINOPHENOL | 0.03 | 0.17 |
| 4-AMINO-m-CRESOL | 0.06 | 0.3 |
| p-AMINOPHENOL | 0.03 | 0.11 |
| 2-amino-5-ethylphenol. HCl | 0.2 | 0.47 |
| 3-(2,5-diaminophenyl)-1-propanol | 0.6 | 1.64 |
| Mineral oil | 60 | 60 |
| POLYQUATERNIUM-67 | 0.19 | 0.19 |
| water | qs 100% | qs 100% |
| STEARETH-2 | 1.13 | 1.13 |
| STEARETH-20 | 3.88 | 3.88 |
| CAPRYLYL/CAPRYL GLUCOSIDE | 2.4 | 2.4 |
| POLYSORBATE 21 | 2.4 | 2.4 |
| Ascorbic Acid | 0.25 | 0.25 |

| Oxidizing composition | Ox1 |
|---|---|
| DIETHYLENETRIAMINEPENTAACETIC ACID | 0.06 |
| HYDROGEN PEROXIDE | 6 |
| DISODIUM TIN HEXAHYDROXIDE | 0.04 |
| TETRASODIUM PYROPHOSPHATE 10 $H_2O$ | 0.03 |
| WATER | qs 100% |
| LIQUID PETROLEUM JELLY | 20 |
| GLYCEROL | 0.5 |
| POLY[(DIMETHYLIMINO)-1,3-PROPANEDIYL(DIMETHYLIMINO)-1,6-HEXANEDIYL DICHLORIDE] | 0.15 |
| POLYDIMETHYLDIALLYLAMMONIUM CHLORIDE | 0.2 |
| OXYETHYLENATED STEARYL ALCOHOL (20 OE) | 5 |
| CETYLSTEARYL ALCOHOL (30/70 C16/C18) | 6 |
| VITAMIN E: DL-ALPHA-ITOCOPHEROL | 0.1 |

The dye compositions 1 and 2 are mixed with the oxidizing formula Ox1 according to the ratio 1+1.

Results Obtained

The mixtures thus obtained are applied to natural hair containing 90% grey hairs. After the leave-on time of 35 minutes at ambient temperature, the hair is rinsed, washed and then dried.

The locks are evaluated visually.

| Formulae | Shades |
|---|---|
| 1 + Ox1 | Light blonde |
| 2 + Ox1 | Light golden chestnut |

Example 2

| Dye composition | Comparative A | Invention B |
|---|---|---|
| SODIUM METABISULFITE | 0.22 | 0.22 |
| ETHANOLAMINE | 5.72 | 5.72 |
| EDTA | 0.2 | 0.2 |
| 2,4-DIAMINOPHENOXYETHANOL HCl | 0.04 | 0.04 |
| 2-METHYLRESORCINOL | 0.38 | 0.38 |
| 4-AMINO-2-HYDROXYTOLUENE | 0.01 | 0.01 |
| 6-HYDROXYINDOLE | 0.13 | 0.13 |
| 2-AMINO-3-HYDROXYPYRIDINE | 0.08 | 0.08 |
| RESORCINOL | $5 \times 10^{-3}$ mol | |
| m-AMINOPHENOL | 0.15 | 0.15 |
| HYDROXYETHOXY AMINOPYRAZOLOPYRIDINE HCL | 0.07 | 0.07 |
| 2-amino-5-ethylphenol. HCl | — | $5 \times 10^{-3}$ mol |
| 3-(2,5-diaminophenyl)-1-propanol | 2.6 | 2.6 |
| MINERAL OIL | 60 | 60 |
| HYDROXYPROPYL GUAR | 1 | 1 |
| WATER | qs 100 | qs 100 |
| PEG-40 HYDROGENATED CASTOR OIL | 1 | 1 |
| COCO-GLUCOSIDE | 3 | 3 |
| SODIUM LAURYL SULFATE | 1.24 | 1.24 |
| ASCORBIC ACID | 0.12 | 0.12 |

| Composition | Oxy 2 |
|---|---|
| PENTASODIUM PENTETATE | 0.06 |
| HYDROGEN PEROXIDE | 6 |
| SODIUM STANNATE | 0.04 |
| PHOSPHORIC ACID | Qs pH = 2 +/− 0.2 |
| TETRASODIUM PYROPHOSPHATE | 0.02 |
| WATER | qs 100 |
| GLYCEROL | 0.5 |
| TRIDECETH-2 CARBOXAMIDE MEA | 0.85 |
| CETEARYL ALCOHOL (and) CETEARETH-25 | 2.85 |

Compositions (A) (comparative) and (B) (invention) are mixed with the oxidizing formula Ox2 according to the ratio 1+1.5.

The mixtures thus obtained are applied to permanent-waved hair containing 90% grey hairs. After a leave-on time of 35 minutes at ambient temperature, the locks are washed with a shampoo, rinsed and then dried.

The locks thus dyed were evaluated after 12 shampooing operations according to the protocol below.

Washing Test (12 sh.)

This test makes it possible to evaluate and quantify the degradation of the artificial colour of locks of hair caused by repeated washing. The dyed hair is washed 12 times with shampoo. The tests were carried out in a machine which automatically links together the 12 washes, the rinses and the drying operations on the dyed locks.

The colour of the locks is evaluated before and after washes by means of a Minolta CM2600D spectrocolorimeter (illuminant D65, observation angle of 10, specular component included) in the CIEL*a*b* system. In this L*a*b* system, the three parameters denote, respectively, the intensity (L*), a* indicates the green/red colour axis and b* the blue/yellow colour axis.

The variation in the colouration of the locks before and after washes is measured (ΔE) according to the following equation:

$$\Delta E = \sqrt{(L^* - L_0^*)^2 + (a^* - a_0^*)^2 + (b^* - b_0^*)^2}$$

In this equation, L*, a* and b* represent the values measured after 12 washes and L0*, a0* and b0* represent the values measured before washes.

The resistance of the dyeing of the hair to the washes is all the better the smaller the difference in colour ΔE of the locks before and after washing. The results are reported in the table below.

|  |  | L* | a* | b* | ΔE |
|---|---|---|---|---|---|
| A + Ox2 | Before sh. | 15.99 | 2.97 | 1.62 | 6.8 |
|  | After 12 sh. | 20.81 | 6 | 5.37 |  |
| B + Ox2 | Before sh. | 14.85 | 2.36 | 1.26 | 4.4 |
|  | After 12 sh. | 19.2 | 2.68 | 1.89 |  |

After 12 shampooing operations, the composition according to the invention results in a much lower ΔE value, thus in a better persistence of the colour than the comparative composition.

Example 3

The following compositions were prepared (amount expressed in g % of active material unless otherwise mentioned).

|  | C1 (invention) | C2 (comparative) |
|---|---|---|
| ETHANOLAMINE | 4.83 | 4.83 |
| 2-AMINO-5-ETHYLPHENOL HCL | 0.41 | 0.41 |
| 6-HYDROXYINDOLE | 0.01 | 0.01 |
| HYDROXYBENZOMORPHOLINE | 0.01 | 0.01 |
| 4-AMINO-2-HYDROXYTOLUENE | 0.04 | 0.04 |
| ASCORBIC ACID | 0.25 | 0.25 |
| EDTA | 0.2 | 0.2 |
| 2-METHYLRESORCINOL | 0.08 | 0.08 |
| CAPRYLYL/CAPRYL GLUCOSIDE | 2.4 | 2.4 |
| POLYQUATERNIUM-67 | 0.19 | 0.19 |
| SODIUM METABISULFITE | 0.45 | 0.45 |
| MINERAL OIL | 59.7 | 59.7 |
| 5-AMINO-6-CHLORO-o-CRESOL | 0.01 | 0.01 |
| STEARETH-2 | 1.13 | 1.13 |
| STEARETH-20 | 3.88 | 3.88 |
| POLYSORBATE 21 | 2.4 | 2.4 |
| HYDROXYETHYL-p-PHENYLENEDIAMINE SULFATE |  | $3.6 \times 10^{-3}$ mol |
| 3-(2,5-DIAMINOPHENYL)PROPAN-1-OL-HCl | $3.6 \times 10^{-3}$ mol |  |
| WATER | qs 100 | qs 100 |

| Oxidizing compositions (in g % of active material) | D |
|---|---|
| Diethylenetriaminepentaacetic acid, pentasodium salt | 0.06 |
| Hydrogen peroxide | 6 |
| Disodium tin hexahydroxide | 0.04 |
| Tetrasodium pyrophosphate decahydrate | 0.03 |
| Liquid petroleum jelly | 20 |
| Poly[(dimethylimino)-1,3-propanediyl(dimethylimino)-1,6-hexanediyl dichloride] | 0.15 |
| Polydimethyldiallylammonium chloride | 0.2 |
| Glycerol | 0.5 |
| Cetylstearyl alcohol (30/70: $C_{16}/C_{18}$) | 6 |
| Oxyethylenated stearyl alcohol (20 OE) | 5 |
| PEG-4 rapeseedamide | 1.2 |
| Vitamin D: DL-alpha-tocopherol | 0.1 |
| Trideceth-2 carboxamide MEA | — |
| Ceteareth-25 | — |
| Phosphoric acid | qs pH = 2.2 ± 0.2 |
| Water | qs 100 |

Compositions C1 and C2 are mixed with the oxidizing composition D in a 1:1 weight ratio.

The mixtures thus obtained, C1+D and C2+D, are applied to locks of natural hair containing 90% grey hairs. After a leave-on time of 35 minutes at ambient temperature, the locks are rinsed with clear water, then washed with a shampoo. Finally, the locks are dried.

The colorimetric measurements are performed using a Minolta CM2006D spectrocolorimeter (illuminant D65, angle 10°, specular components included) in the CIELab system. L* represents the lightness; the lower the value of L*, the more powerful the colouration obtained.

|  | L* |
|---|---|
| C1 + D (invention) | 31.3 |
| C2 + D (comparative) | 33.6 |

The mixture C1+D according to the invention results in a lower value of L*, and thus a more powerful colouration, compared with comparative mixture C2+D.

The locks are then subjected to a test of 12 shampooing operations in order to evaluate the fastness with respect to washing, according to the protocol described above.

The results are reported in the table below.

|  | L* | a* | b* | ΔE |
|---|---|---|---|---|
| C1 + D (invention) before test | 31.3 | 4.6 | 6.9 | 2.3 |
| C1 + D (invention) after test | 32.2 | 5.7 | 8.7 |  |
| C2 + D (comparative) before test | 33.6 | 5.3 | 8.9 | 4.3 |
| C2 + D (comparative) after test | 36.7 | 2.7 | 7.4 |  |

The mixture obtained with composition C1 according to the invention has a lower ΔE value, and thus a better fastness with respect to washing, compared with the mixture obtained with composition C2.

Example 4

The following compositions were prepared (amount expressed in g % of active material unless otherwise mentioned).

|  | C3 (Comparison) | C4 (invention) |
| --- | --- | --- |
| POLYGLYCERYL-2 OLEYL ETHER | 4 | 4 |
| POLYGLYCERYL-4 OLEYL ETHER | 7.692 | 7.692 |
| OLEIC ACID | 3 | 3 |
| PEG-2 OLEAMINE | 7 | 7 |
| SODIUM DIETHYLAMINOPROPYL COCOASPARTAMIDE | 5.45 | 5.45 |
| OLEYL ALCOHOL | 5 | 5 |
| TRIDECETH-2 CARBOXAMIDE MEA | 10 | 10 |
| ALCOHOL DENAT. | 5 | 5 |
| PROPYLENE GLYCOL | 9.7 | 9.7 |
| FRAGRANCE | 0.75 | 0.75 |
| HEXYLENE GLYCOL | 9.3 | 9.3 |
| ERYTHORBIC ACID | 0.18 | 0.18 |
| PENTASODIUM PENTETATE | 2.4 | 2.4 |
| SODIUM METABISULFITE | 0.455 | 0.455 |
| AMMONIUM ACETATE | 0.8 | 0.8 |
| HYDROXYETHYL-p-PHENYLENEDIAMINE SULFATE | $3.6 \times 10^{-3}$ mol | / |
| HYDROXYPROPYL-P-PHENYLENEDIAMINE HCL | / | $3.6 \times 10^{-3}$ mol |
| 2-AMINO-5-ETHYLPHENOL HCL | 0.41 | 0.41 |
| HYDROXYBENZOMORPHOLINE | 0.01 | 0.01 |
| 2-METHYLRESORCINOL | 0.08 | 0.08 |
| 4-AMINO-2-HYDROXYTOLUENE | 0.04 | 0.04 |
| 6-HYDROXYINDOLE | 0.01 | 0.01 |
| 5-AMINO-6-CHLORO-o-CRESOL | 0.01 | 0.01 |
| AMMONIUM HYDROXIDE | 10.2 | 10.2 |
| WATER | 100 | 100 |

| Oxidizing compositions | D4 |
| --- | --- |
| CETEARYL ALCOHOL (and) CETEARETH-25 | 2.85 |
| TRIDECETH-2 CARBOXAMIDE MEA | 0.85 |
| Glycerine | 0.5 |
| TETRASODIUM PYROPHOSPHATE | 0.02 |
| SODIUM STANNATE | 0.04 |
| HYDROGEN PEROXIDE (50%) | 12 |
| Phosphoric acid | Qs pH = 2 ± 0.2 |
| water | Qs 100 |

The compositions C3 and C4 are mixed with the oxidizing composition D4 in a 1:1 weight ratio.

The mixtures thus obtained, C3+D4 and C4+D4, are applied to locks of natural hair containing 90% grey hairs. After a leave-on time of 35 minutes at ambient temperature, the locks are rinsed with clear water, then washed with a shampoo. Finally, the locks are dried.

The colorimetric measurements are performed using a Data color SF600X spectrocolorimeter (illuminant D65, angle 10°, specular components included) in the CIELab system. L* represents the lightness; the lower the value of L*, the more powerful the colouration obtained.

The fastness of the coloration was evaluated by subjecting colored locks to 3 and 6 shampoos. This evaluation is done by calculating the DE as above defined from L*a*b* of colored locks before shampoo, after 3 shampoos and after 6 shampoos.

The results are reported in the table below

|  |  | L* | a | b* | ΔE |
| --- | --- | --- | --- | --- | --- |
| C3 + D4 (comparison) | Before shampoo | 32.6 | 5 | 4.5 | — |
|  | After 3 shampoos | 35.8 | 3.7 | 4.1 | 3.5 |
|  | After 6 shampoos | 34.6 | 3.3 | 3.6 | 3.8 |
| C4 + D4 (invention) | Before shampoos | 30.3 | 3.0 | 1.1 | — |
|  | After 3 shampoos | 30.8 | 2.6 | 1.1 | 0.6 |
|  | After 6 shampoos | 30.7 | 2.8 | 2.1 | 1.1 |

The composition according to the invention exhibits a lower ΔE value than the one obtained from the comparative composition. This shows that the composition of the invention provides a better shampoo resistance.

The invention claimed is:

1. A composition for dyeing keratin fibers, wherein the composition comprises:
   (a) from about 0.005% to about 6% of at least one coupler chosen from 2-amino-5-ethylphenol coupler, addition salts thereof, and/or solvates thereof, and
   (b) from about 0.005% to about 6% of at least one oxidation base chosen from 3-(2,5-diaminophenyl)-1-propanol, addition salts thereof, and/or solvates thereof;
   wherein all the percentages are by weight based on the total weight of the composition.

2. The composition according to claim 1, wherein the at least one coupler is chosen from addition salts of the 2-amino-5-ethylphenol coupler with an acid, wherein the addition salts are chosen from hydrochlorides, hydrobromides, sulfates, citrates, succinates, tartrates, lactates, tosylates, benzenesulfonates, methanesulfonates, phosphates, or acetates.

3. The composition according to claim 1, wherein the at least one coupler is chosen from addition salts of the 2-amino-5-ethylphenol coupler with a base, wherein the base is chosen from sodium hydroxide, potassium hydroxide, ammonia, amines, or alkanolamines.

4. The composition according to claim 1, wherein the solvates of the at least one coupler is chosen from hydrates of the 2-amino-5-ethylphenol coupler and/or of the combination of the 2-amino-5-ethylphenol coupler with a linear or branched $C_1$ to $C_4$ alcohol.

5. The composition according to claim 1, wherein the at least one oxidation base is chosen from addition salts of 3-(2,5-diaminophenyl)-1-propanol with an acid, and wherein the acid is chosen from hydrochlorides, hydrobromides, sulfates, citrates, succinates, tartrates, lactates, tosylates, benzenesulfonates, methanesulfonates, phosphates, or acetates.

6. The composition according to claim 1, wherein the at least one oxidation base is chosen from the addition salts of 3-(2,5-diaminophenyl)-1-propanol with a base, and wherein the base is chosen from sodium hydroxide, potassium hydroxide, ammonia, amines, or alkanolamines.

7. The composition according to claim 1, wherein the solvates of the 3-(2,5-diaminophenyl)-1-propanol are chosen from hydrates of 3-(2,5-diaminophenyl)-1-propanol or a combination of 3-(2,5-diaminophenyl)-1-propanol with a linear or branched $C_1$ to $C_4$ alcohol.

8. The composition according to claim 1, further comprising at least one additional coupler and/or oxidation base.

9. The composition according to claim 1, further comprising at least one surfactant.

10. The composition according to claim 1, further comprising at least one alkaline agent.

11. The composition according to claim 1, further comprising a chemical oxidizing agent.

12. The composition of claim 11, wherein the chemical oxidizing agent is hydrogen peroxide.

13. A method for dyeing keratin fibers, comprising applying to the keratin fibers a composition, wherein the composition comprises:
   (a) from about 0.005% to about 6% of at least one coupler chosen from 2-amino-5-ethylphenol coupler, addition salts thereof, and/or solvates thereof, and
   (b) from about 0.005% to about 6% of at least one oxidation base chosen from 3-(2,5-diaminophenyl)-1-propanol, addition salts thereof, and/or solvates thereof;
   wherein all the percentages are by weight based on the total weight of the composition.

14. A multi-compartment device for dyeing keratin fibers, comprising:
   at least one first compartment comprising a dye composition, wherein the dye composition comprises:
      (a) at least one coupler chosen from 2-amino-5-ethylphenol coupler, addition salts thereof, and/or solvates thereof, present in an amount ranging from about 0.005% to about 6% by weight, relative to the total weight of the dye composition; and
      (b) at least one oxidation base chosen from 3-(2,5-diaminophenyl)-1-propanol, addition salts thereof, or solvates thereof, present in an amount ranging from about 0.005% to about 6% by weight, relative to the total weight of the dye composition; and
   at least one second compartment comprising an oxidizing composition (B), wherein the oxidizing composition (B) comprises at least one chemical oxidizing agent.

* * * * *